US00PP31568P2

(12) United States Plant Patent
Hartman

(10) Patent No.: US PP31,568 P2
(45) Date of Patent: Mar. 17, 2020

(54) ***CALADIUM* PLANT NAMED 'JUST SAUCY'**

(50) Latin Name: ***Caladium* X *hortulanum***
Varietal Denomination: Just Saucy

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/501,040

(22) Filed: Feb. 13, 2019

(51) Int. Cl.
*A01H 5/02* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Caladium* plant named 'Just Saucy', characterized by its intermediate to tall height; upright and mounding plant habit; dense and bushy appearance; vigorous growth habit and rapid growth rate; fancy-type leaves that have dark green-colored margins with greyed green and yellow green-colored venation and centers with white and greyed red-colored interveinal areas and random yellow green-colored speckles and flecks and random greyed red-colored spots and blotches; and leaf petioles that are medium green or medium green flushed with a brown tinge in color.

4 Drawing Sheets

Botanical designation: *Caladium* X *hortulanum*.
Cultivar denomination: 'JUST SAUCY'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'Just Saucy'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of *Caladium* X *hortulanum* 'Miss Muffet', not patented, as the female, or seed, parent with *Caladium* X *hortulanum* 'Twist N' Shout', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2010.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Just Saucy'. These characteristics in combination distinguish 'Just Saucy' as a new and distinct *Caladium* plant:

1. Intermediate to tall in height and upright and mounding plant habit; dense and bushy appearance.
2. Vigorous growth habit and rapid growth rate.
3. Fancy-type leaves that have dark green-colored margins with greyed green and yellow green-colored venation and centers with white and greyed red-colored interveinal areas and random yellow green-colored speckles and flecks and random greyed red-colored spots and blotches.
4. Petioles that are medium green or medium green flushed with a brown tinge in color.

Plants of the new *Caladium* differ primarily from plants of the female parent, 'Miss Muffet', in the following characteristics:

1. Plants of the new *Caladium* are taller than plants of 'Miss Muffet'.
2. Plants of the new *Caladium* and 'Miss Muffet' differ in leaf color as leaves of plants of the new *Caladium* have dark green-colored margins with greyed green and yellow green-colored venation and centers with white and greyed red-colored interveinal areas and random yellow green-colored speckles and flecks and random greyed red-colored spots and blotches whereas leaves of plants of 'Miss Muffet' are pale green tinged with pink in color with a deep reddish pink-colored blush in the center.

Plants of the new *Caladium* differ primarily from plants of the male parent, 'Twist N' Shout', in leaf color as leaves of plants of the new *Caladium* have dark green-colored margins with greyed green and yellow green-colored venation and centers with white and greyed red-colored interveinal areas and random yellow green-colored speckles and flecks and random greyed red-colored spots and blotches whereas leaves of plants of 'Twist N' Shout' are olive green in color with green to coppery bronze-colored venation and coppery orange-colored spots and blotches. In addition, leaves of plants of the new *Caladium* are flatter than and not as undulating as leaves of plants of 'Twist N' Shout'.

Plants of the new *Caladium* can be compared to plants of *Caladium* X *hortulanum* 'Creamsickle', disclosed in U.S. Plant Pat. No. 23,991. In side-by-side comparisons, plants of the new *Caladium* differ primarily from plants of 'Creamsickle' in leaf color as leaves of plants of the new *Caladium* have dark green-colored margins with greyed green and yellow green-colored venation and centers with white and greyed red-colored interveinal areas and random yellow green-colored speckles and flecks and random greyed red-colored spots and blotches whereas leaves of plants of 'Creamsickle' have greyed green-colored venation, greyed green and greyed purple-colored interveinal areas interspersed with dark green-colored sectors and borders. In addition, leaves of plants of the new *Caladium* are flatter than and not as undulating as leaves of plants of 'Creamsickle'.

Plants of the new *Caladium* can be compared to plants of *Caladium* X *hortulanum* 'Mesmerized', disclosed in U.S. Plant Pat. No. 29,545. In side-by-side comparisons, plants of the new *Caladium* differ primarily from plants of 'Mesmerized' in leaf color as leaves of plants of the new *Caladium* have dark green-colored margins with greyed green and yellow green-colored venation and centers with white and greyed red-colored interveinal areas and random yellow green-colored speckles and flecks and random greyed red-colored spots and blotches whereas leaves of plants of 'Mesmerized' are variegated with variable areas that are dark green, red orange, whitish green and white in color; with development, mature leaves are mostly dark green in color with variable areas of variegation and interveinal areas with variably coalescing red orange-colored spots and splotches. In addition, leaves of plants of the new *Caladium* are flatter than and not as undulating as leaves of plants of 'Mesmerized'.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Just Saucy' in a container and grown in a shadehouse (tuber not de-eyed).

The photograph at the top of the second sheet is a comparison view of typical plants of 'Just Saucy' grown in containers; the plant on the left has not had its tuber de-eyed and the plant on the right has had its tuber de-eyed prior to planting.

The photograph at the bottom of the second sheet is a side perspective view of typical plants of 'Just Saucy' grown in an open production field.

The photograph at the top of the third sheet is a comparison view of typical potted plants of the female parent, 'Miss Muffet' (left), 'Just Saucy' (center) and the male parent, 'Twist N' Shout' (right).

The photograph at the bottom of the third sheet is a comparison view of typical potted plants of 'Mesmerized' (left), 'Just Saucy' (center) and 'Creamsickle' (right).

The photograph at the top of the fourth sheet is a close-up view of typical freshly-harvested tubers with roots and leaf petioles of 'Just Saucy'.

The photograph at the bottom of the fourth sheet is a close-up view of a typical inflorescence of 'Just Saucy'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were ten weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Just Saucy'.

Parentage:

*Female, or seed, parent.*—*Caladium* X *hortulanum* 'Miss Muffet', not patented.

*Male, or pollen, parent.*—*Caladium* X *hortulanum* 'Twist N' Shout', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments elliptic and irregular in shape. Height: About 3.7 cm to 4.1 cm. Diameter: About 5.5 cm to 11.6 cm. Segment height: About 2.6 cm. Segment diameter: About 2.6 cm. Axillary bud size: About 3.5 mm by 3.5 mm. Texture: Thick, starchy; somewhat brittle. Color: Epidermis, freshly-harvested: Close to 56C and 49C to 49D. Epidermis, dried: Close to 200A. Cortical tissue: Close to 155D. Axillary buds: Close to 36A and 37D. Root description: Thick, fleshy contractile roots with few lateral branches; color, close to N155D. Rooting habit: Medium density to dense.

Plant description:

*Plant type*.—Herbaceous perennial; suitable as a potted plant in containers 15-cm to 25-cm and suitable as a landscape plant in shaded areas.

*Plant and growth habit*.—Intermediate to tall in height and upright to mounded plant habit; inverted triangle and wider than tall; dense and bushy appearance; vigorous growth habit and rapid growth rate; potted plants finish in saleable form in about seven to eight weeks after planting tubers; leaf petioles and leaves arise from one or more growing points on tubers; leaf petioles initially upright and outwardly leaning with development.

*Plant height, from soil level to top of foliar plane, shadehouse-grown potted plants*.—About 31 cm to 38 cm.

*Plant height, from soil level to top of inflorescences, shadehouse-grown potted plants*.—About 37.7 cm.

*Plant diameter or spread, shadehouse-grown potted plants*.—About 41 cm to 46 cm.

*Number of shoots per plant, shadehouse-grown potted plants, tubers not de-eyed*.—About four to five develop per #1 tuber.

*Number of shoots per plant, shadehouse-grown potted plants, tubers de-eyed*.—About five to six develop per #1 tuber.

*Cataphylls, shadehouse-grown potted plants*.—Length: About 6 cm to 13.2 cm. Width: About 1.6 cm to 1.9 cm. Shape: Lanceolate or ligulate. Apex: Acute, cuspidate or acuminate. Base: Sheathing the stem. Color, inner surface: Close to N155C; colors and patterns on the outer surface are visible on the inner surface. Color, outer surface: Close to 147A to 147B stippled, streaked and tessellated with close to 200A to 200B; with development, color becoming closer to 200C stained with 187B.

Leaf description:

*Arrangement and type*.—Alternate; simple; fancy-type.

*Length, shadehouse-grown potted plants*.—About 19 cm to 24 cm.

*Width, shadehouse-grown potted plants*.—About 12.5 cm to 14.3 cm; when flattened, about 13 cm to 15 cm.

*Shape*.—Ovate to slightly obovate.

*Apex*.—Acute to acuminate.

*Base*.—Sagittate to peltate.

*Margin*.—Entire; undulate with broad undulations.

*Texture and luster, upper surface*.—Rugose, glabrous; dull.

*Texture and luster, lower surface*.—Slightly rugose, glabrous; slightly glaucous; dull sheen.

*Venation pattern*.—Pinnate.

*Color, shadehouse-grown potted plants*.—Developing and fully developed leaves, upper surface: Towards the margins: Close to 147A. Leaf edge: Close to 147A. Basal notch: Close to 187A. Midvein and primary venation: Close to 149D and 194C; at the petiole attachment, may or may not tinged with 187A; areas surrounding venation, close to 155C and 149D. Interveinal areas: Close to 145C, 145D or 147D with speckles and flecks, close to 147B and 147C; or close to 178B to 178C. Random spots and blotches: Close to 178A. Developing and fully developed leaves, lower surface: Background color: Darker than 191A. Leaf edge: Close to 191A. Basal notch: Close to 187B. Midvein: Close to 147C and 147D tinged with 145D; proximally, faintly flushed with 182B to 182C; areas surrounding midvein, close to 155C. Primary venation: Close to 147D tinged with 145D; areas surrounding primary venation, close to 155C. Interveinal areas: Close to 145D and 149D with speckles and flecks, close to 137C and 137D. Random spots and blotches: Close to 182C.

*Petioles*.—Aspect: Initially upright and straight and outwardly leaning with development; flexible. Length, shadehouse-grown potted plants: About 23 cm to 28 cm. Diameter, distally, shadehouse-grown potted plants: About 3.5 mm to 5 mm. Diameter, proximally, shadehouse-grown potted plants: About 6.5 mm to 7 mm. Texture and luster: Smooth, glabrous; dull; just below leaf junction, slightly glaucous. Color, shadehouse-grown potted plants, when developing and fully developed: Proximally, close to 147C flushed with 147A with faint stippling and streaks, close to 147B; may be faintly tinged with 200C; distally (just below leaf junction), similar to proximal colors but may be tinged with close to 181C to 181D. Wing length, shadehouse-grown potted plants: About 4.6 cm to 7.5 cm. Wing diameter, shadehouse-grown potted plants: About 6 mm to 8.5 mm. Texture and luster, inner and outer surfaces: Smooth, glabrous; dull. Wing color, shadehouse-grown potted plants: Inner surface: Close to 155C; colors and patterns on the outer surface are visible on the inner surface. Outer surface: Close to 147B and 147C faintly stippled, streaked and tessellated with 200A.

Inflorescence description: Inflorescences observed on four week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor notes.

*Natural flowering season and flower longevity*.—Plants of the new *Caladium* typically flower during the spring and summer in central Florida; flowers develop about four weeks after growth commences; inflorescences last about three days before fading; inflorescences persistent.

*Spathe*.—Length, overall: About 12.7 cm. Length, distal open portion: About 7.7 cm. Length, proximal closed portion: About 5 cm. Width, distal open portion: About 4.5 cm. Depth, distal open portion: About 1.8 cm. Width, at constriction: About 1.3 cm. Width, proximal closed portion: About 3 cm. Shape, open portion: Broadly elliptic, rounded. Apex: Acuminate. Base: Acute. Margin: Entire; smooth. Texture and luster, front surface: Smooth, glabrous; dull. Texture and luster, rear surface: Smooth, glabrous; dull; proximally, glaucous. Color, front surface: Distal open portion: Close to 155C; with development, color becoming closer to 199B to 199C. Proximal closed portion: Distally, close to 147C; towards the base, flushed with close to 187A; color does not change with development. Color, rear surface: Distal open portion: Close to 155C; center tinged with close to 145D; with development, color becoming closer to 199B and N200A. Proximal closed portion: Close to 147B and 147C; color does not change with development.

*Spadix*.—Length, overall: About 7.8 cm. Length, male flower zone: About 4.4 cm. Length, sterile zone: About 1.9 cm. Length, female flower zone: About 1.5 cm. Diameter, male flower zone: About 1 cm. Diameter, sterile flower zone: About 6 mm. Diameter, female flower zone: About 1 cm. Shape: Columnar, spindle-shaped. Apex: Acute. Base: Obtuse. Aspect: Upright. Color, mature, male zone: Close to 158D. Color, mature, sterile zone: Close to 158D. Color, mature, female zone: Close to 159D. Male flowers: Quantity per spadix: About 208. Shape: Obovate. Height: About 3.5 mm. Diameter: About 3.5 mm. Pollen amount: Abundant. Pollen color: Close to 12D. Female flowers: Quantity per spadix: About 204. Shape: Obovate. Height: About 2.5 mm. Diameter: About 2.5 mm. Stigma color: Close to 159D. Ovary color: Close to 161D.

*Scape*.—Length: About 25 cm. Diameter: About 6 mm. Strength: Sturdy; flexible. Aspect: Mostly erect. Texture and luster: Smooth, glabrous; dull; distally, glaucous. Color: Close to 147C faintly stippled and streaked with 147B; distally, close to 147C faintly tinged with 146C.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'Just Saucy' as illustrated and described.

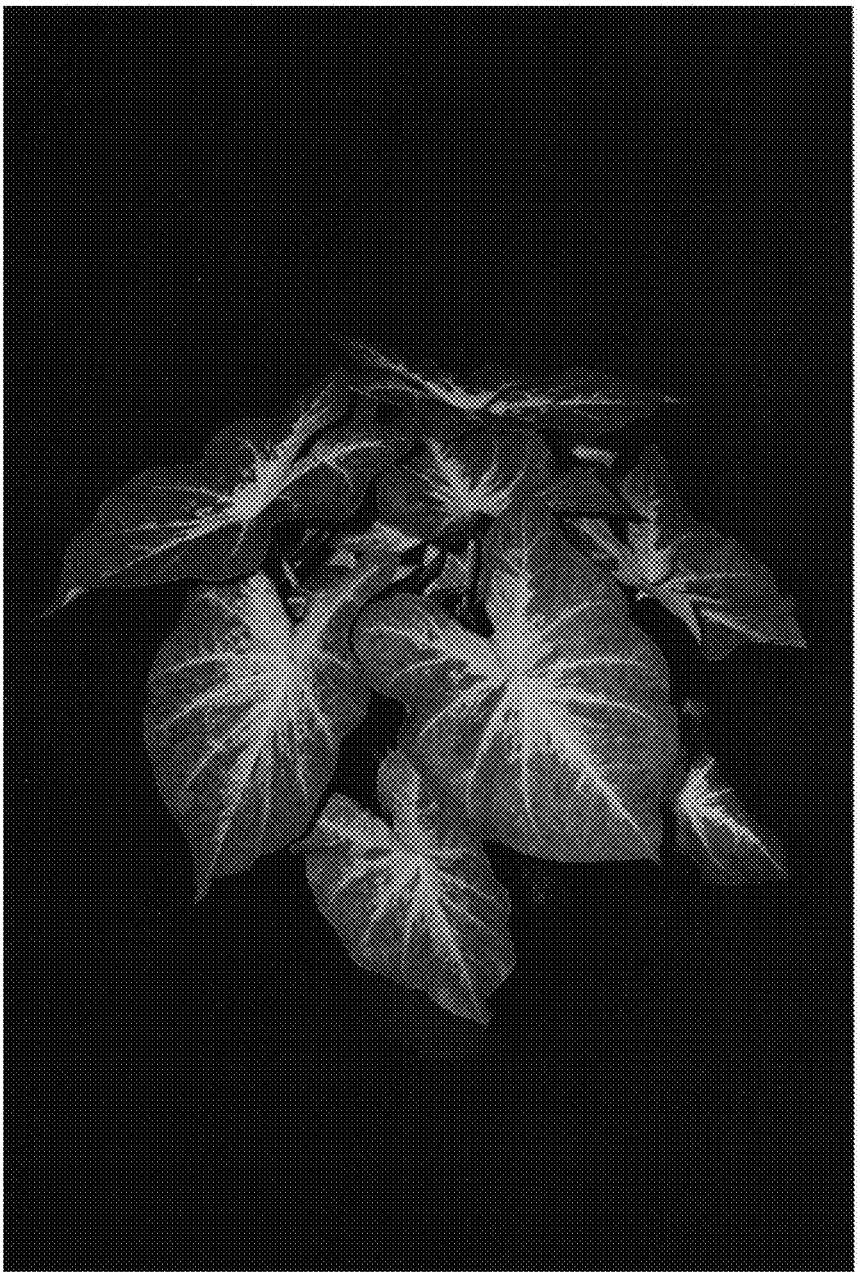

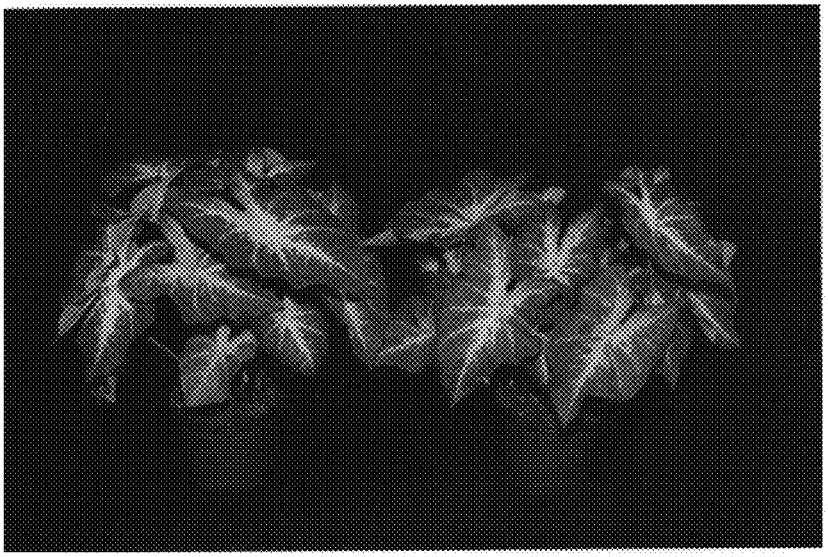
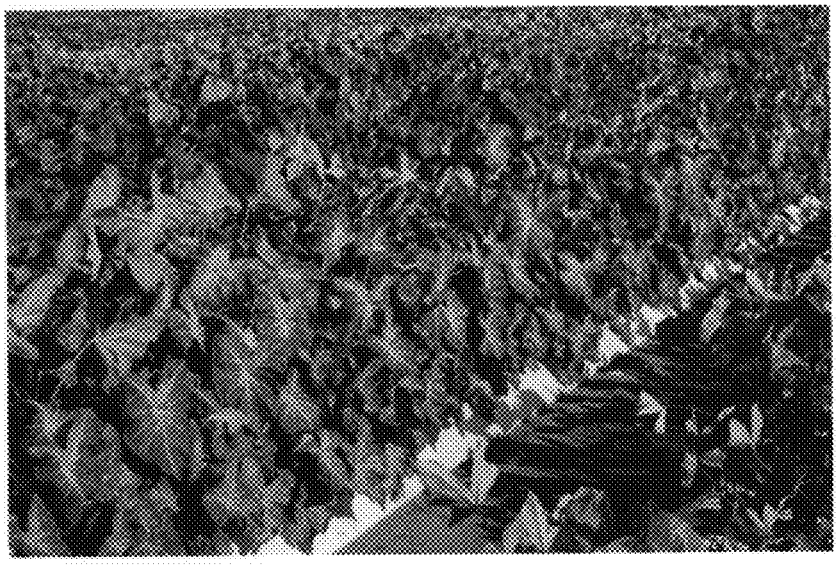

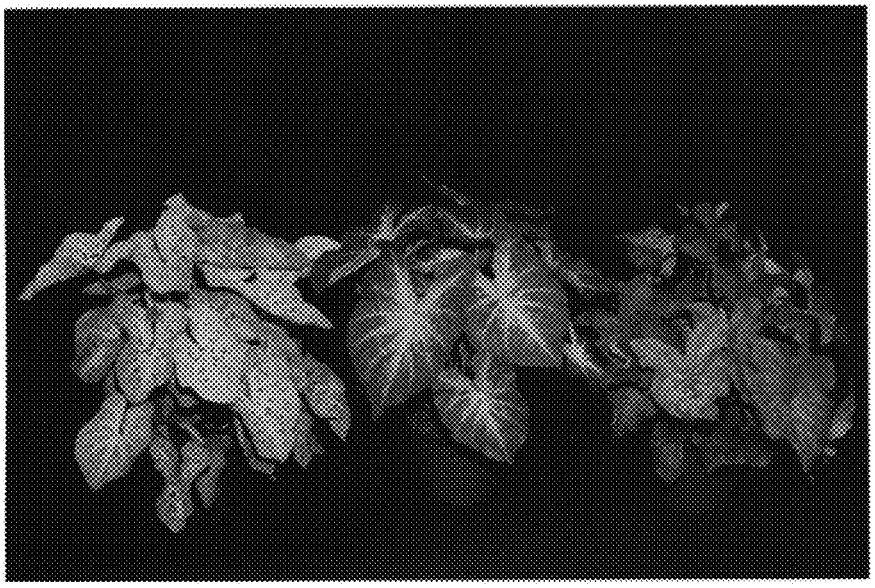
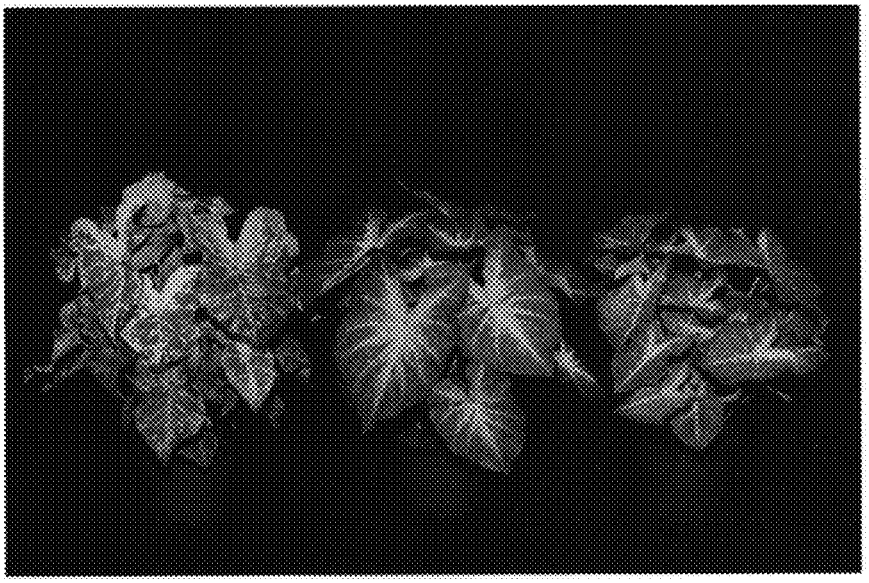

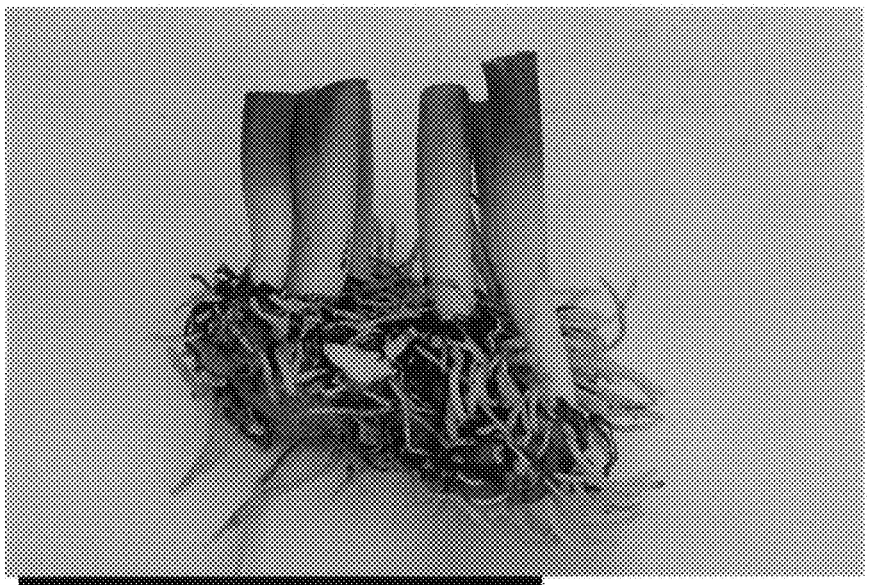
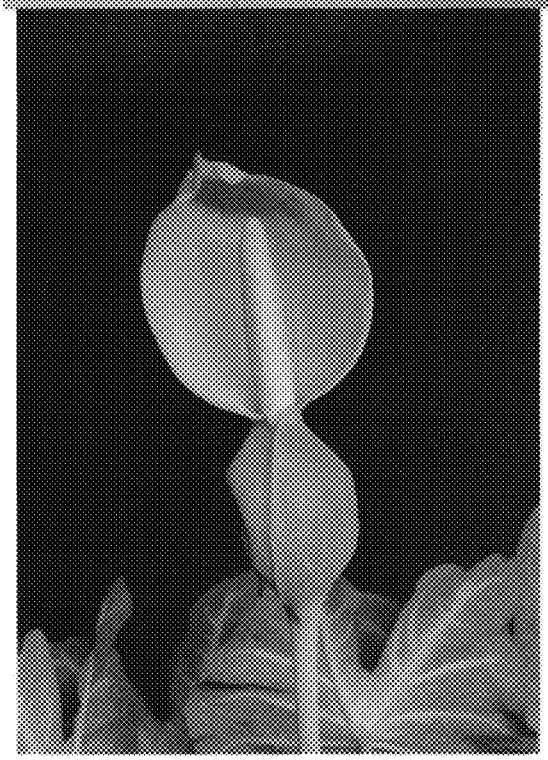

* * * * *